United States Patent
Shieh et al.

(10) Patent No.: US 9,376,453 B2
(45) Date of Patent: Jun. 28, 2016

(54) PREPARATION METHOD OF ZEOLITIC IMIDAZOLATE FRAMEWORK-90 IN WATER-BASED SYSTEM

(71) Applicant: National Central University, Taoyuan County (TW)

(72) Inventors: Fa-Kuen Shieh, Taoyuan County (TW); Shao-Chun Wang, Kaohsiung (TW)

(73) Assignee: NATIONAL CENTRAL UNIVERSITY, Jhongli, Taoyuan County (TW)

( * ) Notice: Subject to any disclaimer, the term of this patent is extended or adjusted under 35 U.S.C. 154(b) by 27 days.

(21) Appl. No.: 14/323,700

(22) Filed: Jul. 3, 2014

(65) Prior Publication Data

US 2015/0191491 A1    Jul. 9, 2015

(30) Foreign Application Priority Data

Jan. 3, 2014    (TW) .............................. 103100164 A

(51) Int. Cl.
  *C07F 3/00*    (2006.01)
  *B01D 53/02*    (2006.01)

(52) U.S. Cl.
  CPC ................. *C07F 3/003* (2013.01); *B01D 53/02* (2013.01); *B01D 2253/204* (2013.01); *B01D 2257/504* (2013.01); *Y10T 428/2982* (2015.01)

(58) Field of Classification Search
  CPC ...................................................... C07F 3/003
  See application file for complete search history.

(56) References Cited

FOREIGN PATENT DOCUMENTS

CN    102993221 A    3/2013

OTHER PUBLICATIONS

Morris et al. "Crystals as Molecules: Postsynthesis Covalent Functionalization of Zeolitic Imidazolate Frameworks" Journal of the American Chemical Society, 2008, vol. 130, pp. 12626-12627.*
Pan et al. "Rapid synthesis of zeolitic imidazolate framework-8 (ZIF-8) nanocrystals in an aqueous system" Chemical Communications, 2011, pp. 2071-2073.*
Shieh, Fa-Kuen et al., Water-Based Synthesis of Zeolitic Imidazolate Framework-90 (ZIF-90) with a Controllable Particle Size, Chemistry A European Journal, Jul. 5, 2013, pp. 11139-11142, vol. 19.

* cited by examiner

*Primary Examiner* — Joseph Kosack
(74) *Attorney, Agent, or Firm* — Muncy, Geissler, Olds & Lowe, P.C.

(57) ABSTRACT

The present invention provides a preparation method of Zeolitic Imidazolate Framework-90 (ZIF-90) in water-based system, which uses pure water as a solvent, and the reaction is carried out at room temperature. In addition, the present invention provides a preparation method of ZIF-90, and the particle size and the uniformity of the obtained ZIF-90 are controllable by addition of adjuvant or additive (Polyvinylpyrrolidone).

7 Claims, 7 Drawing Sheets

PREPARATION METHOD OF ZEOLITIC IMIDAZOLATE FRAMEWORK-90 IN WATER-BASED SYSTEM

CROSS REFERENCE TO RELATED APPLICATION

This application claims the benefits of the Taiwan Patent Application Serial Number 103100164, filed on Jan. 3, 2014, the subject matter of which is incorporated herein by reference.

BACKGROUND OF THE INVENTION

1. Field of the Invention

The present invention relates to a preparation method of Zeolitic Imidazolate Framework-90 (ZIF-90) in water-based system and, more particularly, to a preparation method of ZIF-90 using water as solvent.

2. Description of Related Art

Metal-organic Frameworks (MOFs) is a novel organic-inorganic hybrid material which has an inorganic metal functioning as the center, and has organic functional groups covalently or ionically bonded to the inorganic metal to form a regular porous structure. Most of the MOFs have high porosity and high specific surface area, thus the MOFs have high gas adsorption capacity. According to the different porous size of the MOFs, it can be used as a filter for gaseous molecules having different sizes.

Zeolitic Imidazolate Frameworks (ZIFs) is an MOFs material with high thermal stability. The porous size of the ZIFs can be controlled via surface modification or the type of the modified functional groups on the surface of ZIFs, and thus giving different physical and chemical properties to the material. Therefore, the ZIFs can be further applied in the fields of gas storage, catalysis, molecule separation, or other applications.

Among the ZIFs, Zeolitic Imidazolate Framework-90 (ZIF-90) has carbon-oxygen double bonds which provide good non-covalent attraction between carbon dioxide. In addition, the pore size of ZIF-90 is about 0.35 nm, which is more beneficial for $CO_2$ selection and for the absorption of $CO_2$ to mitigate the environmental impact for greenhouse gases. Moreover, according to the relevant researches, 83 liter of gaseous $CO_2$ can be absorbed by 1 liter of ZIF-90. Moreover, ZIF-90 is non-toxic and easy to be produced. Thus, ZIF-90 is considered as a potential material for absorbing $CO_2$.

However, organic solvents are often used in most of the current conventional preparatory methods for ZIF-90, and the waste produced by mass production of ZIF-90 also becomes a burden to the environment. Therefore, in order to meet the requirements of green chemistry process, a novel preparation method of ZIFs is needed for mass production of ZIF-90, in which the ZIF-90 is synthesized under aqueous conditions, and the environmental pollution caused during preparation is significantly reduced.

The present invention provides a preparation method of Zeolitic Imidazolate Framework-90 (ZIF-90) in water-based system, which is different from the conventional preparation methods that use organic solvent, such as DMF or DEF, and thus significantly reduced the impact to the environment.

SUMMARY OF THE INVENTION

The present invention provides a preparation method of Zeolitic Imidazolate Framework-90 (ZIF-90) in water-based system, which uses water as a solvent and the preparation is carried out at room temperature. Moreover, in the preparation method of the present invention, a particle size of ZIF-90 and its size uniformity can be adjusted by adding an additive such as polyvinylpyrrolidone (PVP) or an auxiliary agent such as $C_{1-6}$ alcohol.

In the present invention, the preparation method of zeolitic imidazolate framework-90 (ZIF-90) in water-based system, comprising: mixing a first solution comprising a zinc compound and a second solution comprising an imidazole compound at room temperature to provide a reactive solution; and reacting the reactive solution to obtain a zeolitic imidazolate framework.

In the preparation method of the present invention, the zinc compound that used in the first solution is soluble in water and is capable to ionize in the water to provide zinc ion. The zinc compound is preferred to be at least one selected from the group consisting of $Zn(NO_3)_2$, $Zn(OH)_2$, $Zn(Ac)_2$, and $ZnCl_2$, and the concentration of the zinc compound in the first solution may be 0.02 to 0.8 M, wherein 0.05 to 0.5 M is preferred.

Further, in the preparation method of the present invention, the imidazole compound in the second solution may be imidazole-2-carboxaldehyde (ICA), and the concentration of the imidazole compound in the second solution may be 0.1 to 1 M, wherein 0.2 to 0.5 M is preferred.

Furthermore, in the preparation method of the present invention, during the reacting process of mixing the first solution and the second solution, a molar ratio of a zinc ion ionized from the zinc compound to the imidazole compound may be 1:1 to 1:80, wherein 1:4 to 1:10 is preferred.

In addition, according to an embodiment of the present invention, the first solution may further comprise an auxiliary agent, the auxiliary agent may be at least one selected from $C_{1-6}$ alcohol, wherein the auxiliary agent is preferred to be at least one selected from the group consisting of ethanol, isopropanol, isobutyl alcohol and tert-butyl alcohol. When the auxiliary agent is added to the first solution, the content of the auxiliary agent in the first solution may be 50% to 100%, and is preferred to be 75% to 100%, wherein water is served as the solvent for the first solution.

In the other embodiment of the present invention, the second solution may further comprise an additive, wherein the additive is polyvinylpyrrolidone (PVP). The content of the additive in the reactive solution may be 0.1 to 10 wt %, wherein 0.2 to 5 wt % is preferred. Further, the molecular weight of the additive PVP is preferred to be 30,000 to 60,000.

In the preparation method of the present invention, the reaction may be carried out at room temperature, and the reaction time may be 1 to 60 minutes, wherein 5 to 10 minutes is preferred.

ZIF-90 provided by the preparation method of the present invention has an average particle size of 100 to 4000 nm, wherein 150 to 3000 nm is preferred. Therefore, nano-scaled ZIF-90 particles may be obtained by the preparation method provided by the present invention, and the surface area of ZIF-90 is significantly increased because the smaller size thereof, thus the absorption efficiency of $CO_2$ can be largely improved while applying the ZIF-90 for the absorption of $CO_2$.

DETAILED DESCRIPTION OF THE PREFERRED EMBODIMENT

Example 1

Figure 1:
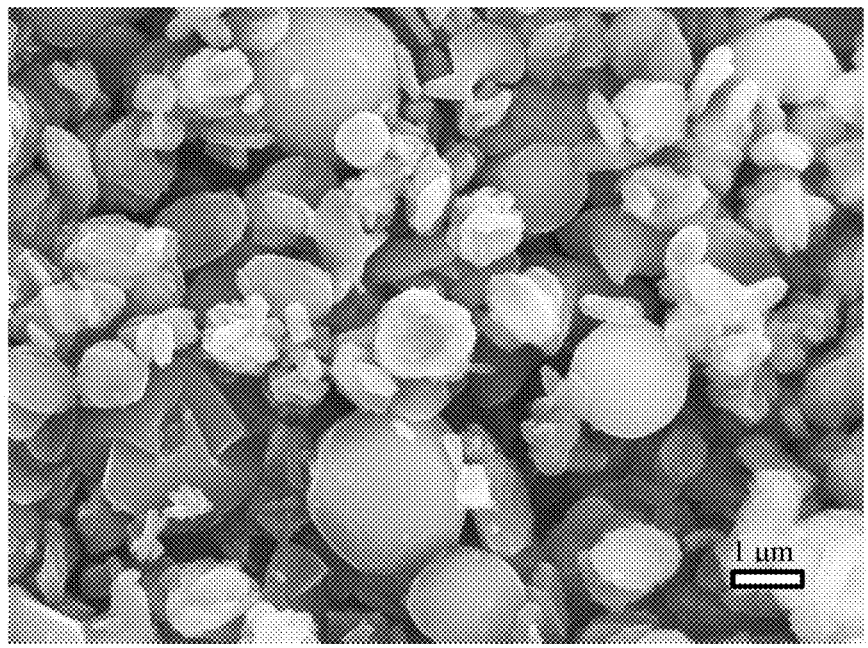
FIG. 1 is a SEM image of ZIF-90 synthesized by example 1 of the present invention.

Zinc nitrate (371 mg) is added into deionized water (3.0 mL) as a first solution. ICA (480 mg) is added into deionized water (25.0 mL) as a second solution. Then, the first solution is gradually added into the second solution at room temperature, and the mixed solution is stirred and reacted to obtain a precipitate powder. In the present example, the molar ratio of $Zn^{2+}$:ICA is 1:4. The resulting powder is collected by centrifugation, washed with methanol, and vacuum dried at 50° C. to obtain ZIF-90 (130 mg). The SEM image of the obtained ZIF-90 is shown in FIG. 1.

Example 2

Zinc nitrate (371 mg) is added into deionized water (3.0 mL) as a first solution. ICA (480 mg) and PVP (500 mg) were added into deionized water (25.0 mL) as a second solution. Then, the first solution is gradually added into the second solution at room temperature, and the mixed solution is stirred and reacted to obtain a precipitate powder. In the present example, the molar ratio of $Zn^{2+}$:ICA is 1:4. The resulting powder is collected by centrifugation, washed with methanol several times, and vacuum dried at 50° C. to obtain ZIF-90 (130 mg). The SEM image of the obtained ZIF-90 with particle size of 2400 nm is shown in FIG. 2.

Figure 2:
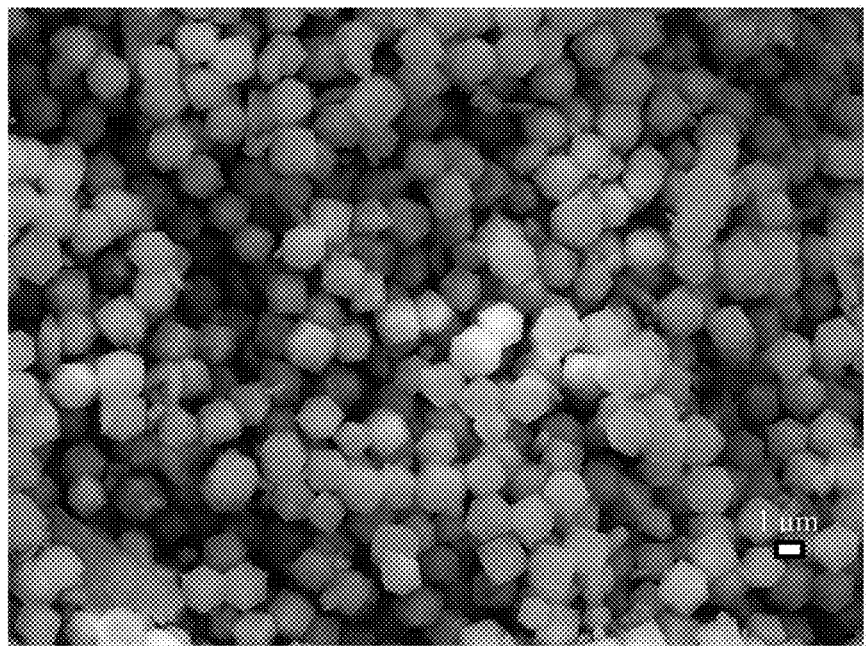
FIG. 2 is SEM image of ZIF-90 synthesized by example 2 of the present invention.

In comparison of the morphology of ZIF-90 prepared by example 1 and example 2, ZIF-90 synthesized with the addition of PVP as the additive in example 2 exhibited uniform particle size (refer to FIG. 2). In the contrast, ZIF-90 synthesized without adding additive in example 1 exhibited non-uniform particle size, and the morphology of the synthesized ZIF-90 is irregular (refer to FIG. 1). Therefore, the uniformity of the ZIF-90 synthesized by the present invention can be greatly improved by adding PVP as additive. In addition, the content of PVP added in example 2 is 2 wt % based on the reactive solution. However, in the other embodiments, the content of PVP may be ranging from 0.1 wt % to 10 wt % based on the reactive solution, wherein 0.2 wt % to 5 wt % is preferred.

Example 3

Figure 3:
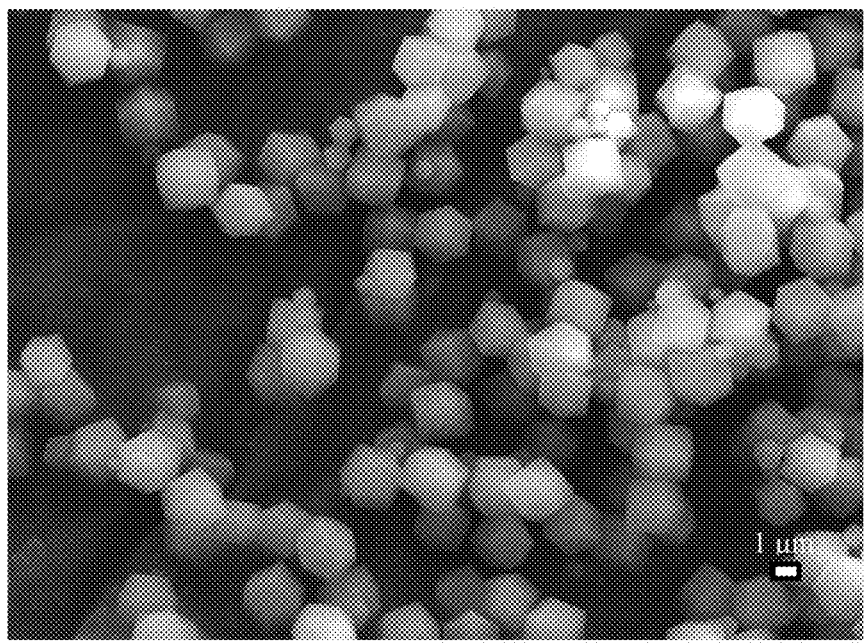
FIG. 3 is SEM image of ZIF-90 synthesized by example 3 of the present invention.

Zinc nitrate (148 mg) is added into deionized water (3.0 mL) as a first solution. ICA (480 mg) and PVP (500 mg) were added into deionized water (25.0 mL) as a second solution. Then, the first solution is gradually added into the second solution at room temperature, and the mixed solution is stirred and reacted to obtain a precipitate powder. In the present example, the molar ratio of $Zn^{2+}$:ICA is 1:10. The resulting powder is collected by centrifugation, washed with methanol several times, and vacuum dried at 50° C. to obtain ZIF-90 (70 mg). The SEM image of the obtained ZIF-90 with particle size of 2600 nm is shown in FIG. 3.

Example 4

Figure 4:
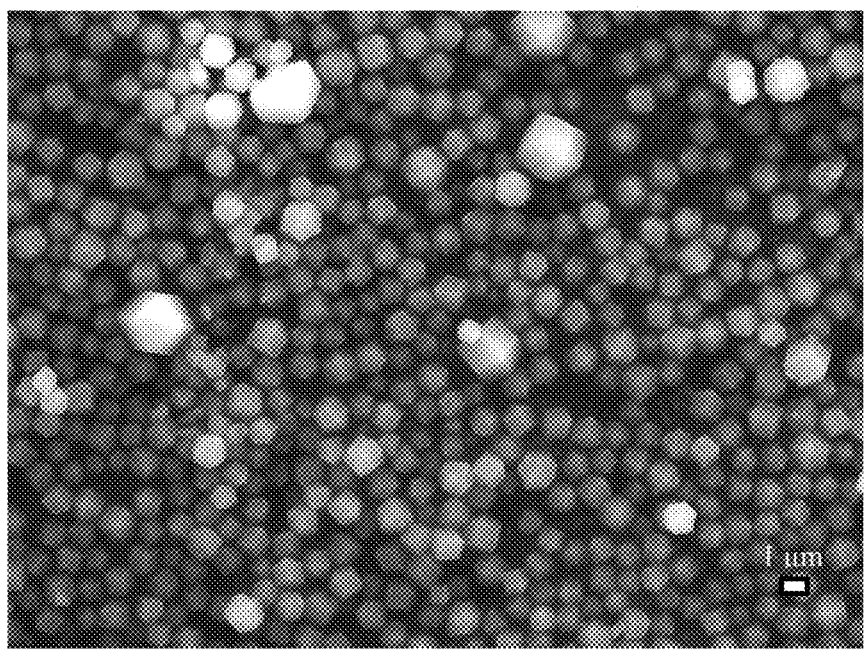
FIG. 4 is SEM image of ZIF-90 synthesized by example 4 of the present invention.

Zinc nitrate (37 mg) is added into deionized water (3.0 mL) as a first solution. ICA (480 mg) and PVP (500 mg) were added into deionized water (25.0 mL) as a second solution. Then, the first solution is gradually added into the second solution at room temperature, and the mixed solution is stirred and reacted to obtain a precipitate powder. In the present example, the molar ratio of $Zn^{2+}$:ICA is 1:40. The resulting powder is collected by centrifugation, washed with methanol several times, and vacuum dried at 50° C. to obtain ZIF-90 (20 mg). The SEM image of the obtained ZIF-90 with particle size of 1500 nm is shown in FIG. 4.

Example 5

Figure 5:
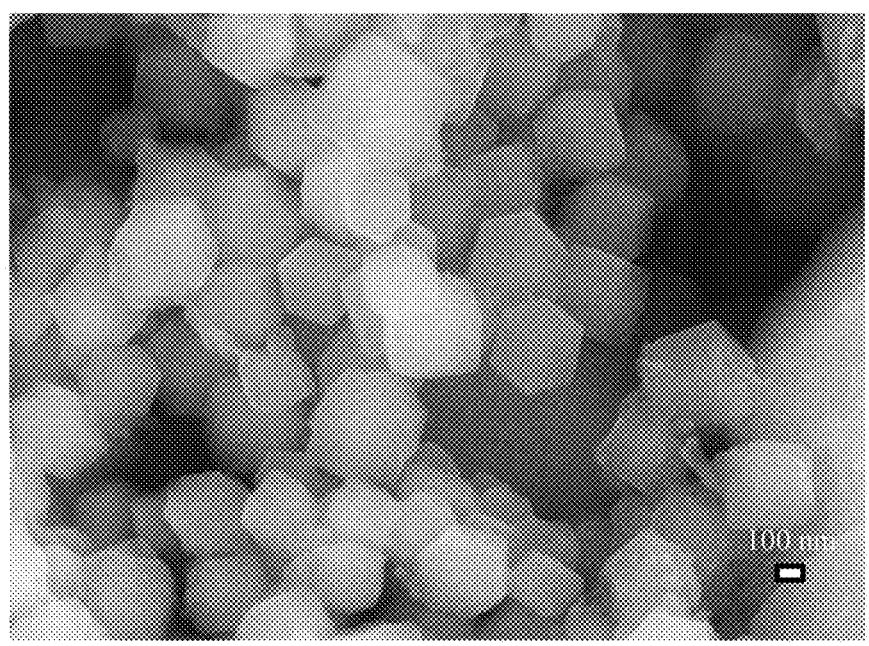
FIG. 5 is SEM image of ZIF-90 synthesized by example 5 of the present invention.

Zinc nitrate (25 mg) is added into deionized water (3.0 mL) as a first solution. ICA (480 mg) and PVP (500 mg) were added into deionized water (25.0 mL) as a second solution. Then, the first solution is gradually added into the second solution at room temperature, and the mixed solution is stirred and reacted to obtain a precipitate powder. In the present example, the molar ratio of $Zn^{2+}$:ICA is 1:60. The resulting powder is collected by centrifugation, washed with methanol several times, and vacuum dried at 50° C. to obtain ZIF-90 (10 mg). The SEM image of the obtained ZIF-90 with particle size of 450 nm is shown in FIG. 5.

Figure 6:
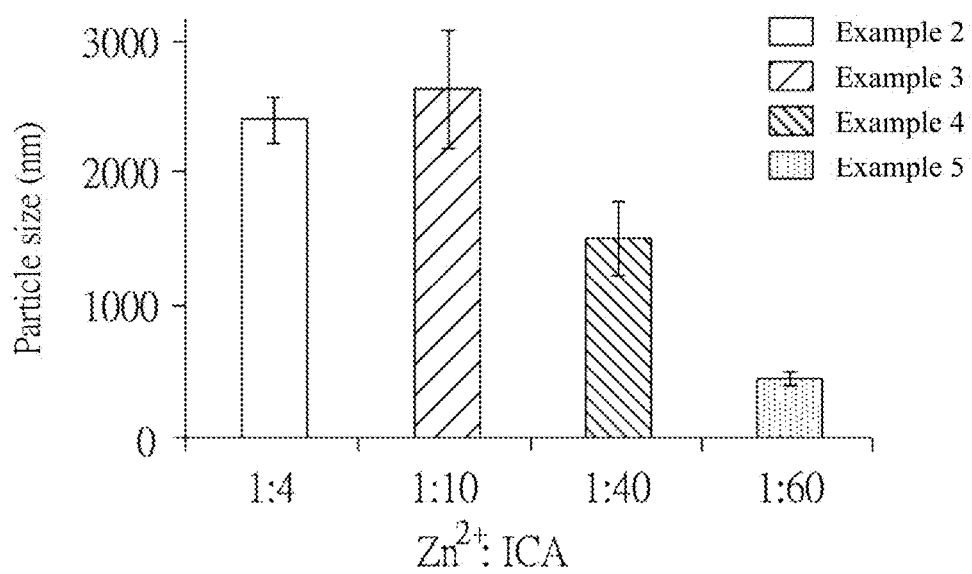
FIG. 6 is a diagram of average particle size of ZIF-90 synthesized in example 2 to example 5 of the present invention.

FIG. 6 shows the corresponding diagram of ZIF-90 synthesized in different molar ratio of $Zn^{2+}$ to ICA ($Zn^{2+}$/ICA) to particle sizes of the synthesized ZIF-90 according to example 2 to example 5 in the present invention, wherein the particle sizes of ZIF-90 is calculated based on the SEM images thereof. According to FIG. 6, the particle size of ZIF-90 changes with the molar ratio of $Zn^{2+}$ to ICA. For example, when the ratio of $Zn^{2+}$/ICA is 1:4 (example 2), the average particle size of ZIF-90 is about 2400 nm, and when the ratio of $Zn^{2+}$/ICA is 1:10, the average particle size of ZIF-90 increased to 2600 nm. Then, the particle size of ZIF-90 decreased when the content of ICA increased, for example, when the ratio of $Zn^{2+}$/ICA is 1:40, the average particle size of the synthesized ZIF-90 is about 1500 nm, and when the ratio of $Zn^{2+}$/ICA is 1:60, the average particle size of the synthesized ZIF-90 is decreased to 450 nm. Therefore, according to the results of examples described above, it is realized that the particle size of the synthesized ZIF-90 can be controlled by the molar ratio of $Zn^{2+}$/ICA.

Example 6

Figure 7:
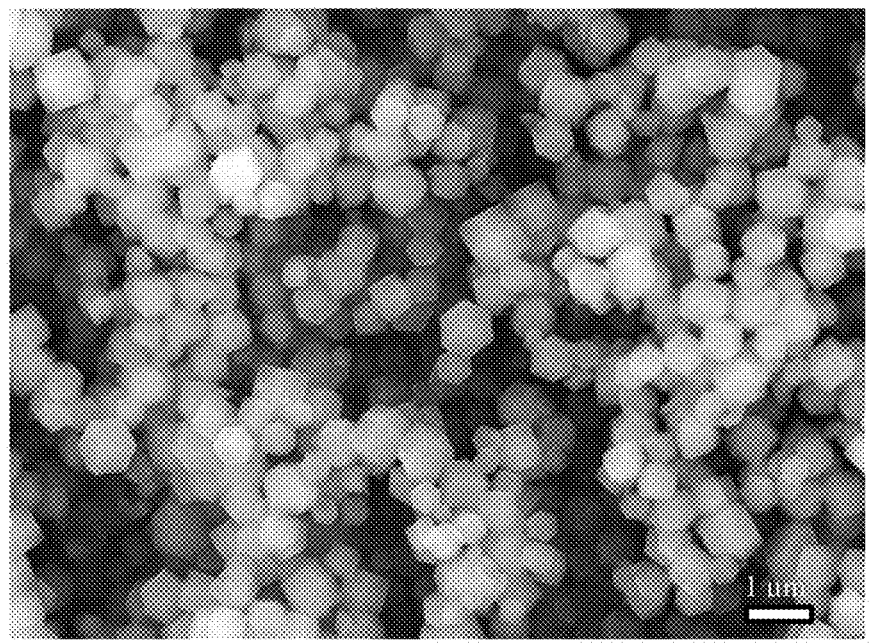
FIG. 7 is SEM image of ZIF-90 synthesized by example 6 of the present invention.

Zinc nitrate (371 mg) is dissolved in ethanol (12.5 mL) as a first solution, wherein ethanol is served as an auxiliary agent. ICA (480 mg) and PVP (500 mg) were added into deionized water (12.5 mL) as a second solution. Then, the first solution is gradually added into the second solution at room temperature, and the mixed solution is stirred and reacted to obtain a precipitate powder. In the present example, the molar ratio of $Zn^{2+}$:ICA is 1:4. The resulting powder is collected by centrifugation, washed with methanol several times, and vacuum dried at 50° C. to obtain ZIF-90 (70 mg). The SEM image of the obtained ZIF-90 with particle size of 610 nm is shown in FIG. 7.

Example 7

Figure 8:
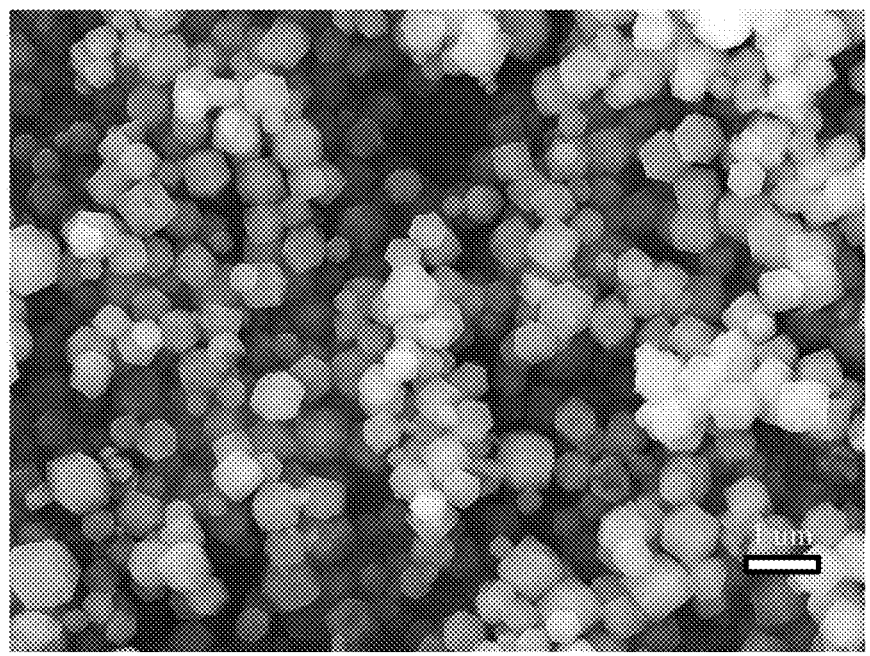
FIG. 8 is SEM image of ZIF-90 synthesized by example 7 of the present invention.

Zinc nitrate (371 mg) is dissolved in isopropanol (12.5 mL) as a first solution, wherein isopropanol is served as an auxiliary agent. ICA (480 mg) and PVP (500 mg) were added into deionized water (12.5 mL) as a second solution. Then, the first solution is gradually added into the second solution at room temperature, and the mixed solution is stirred and reacted to obtain a precipitate powder. In the present example, the molar ratio of $Zn^{2+}$:ICA is 1:4. The resulting powder is collected by centrifugation, washed with methanol several times, and vacuum dried at 50° C. to obtain ZIF-90 (70 g). The SEM image of the obtained ZIF-90 with particle size of 600 nm is shown in FIG. 8.

Example 8

Figure 9:
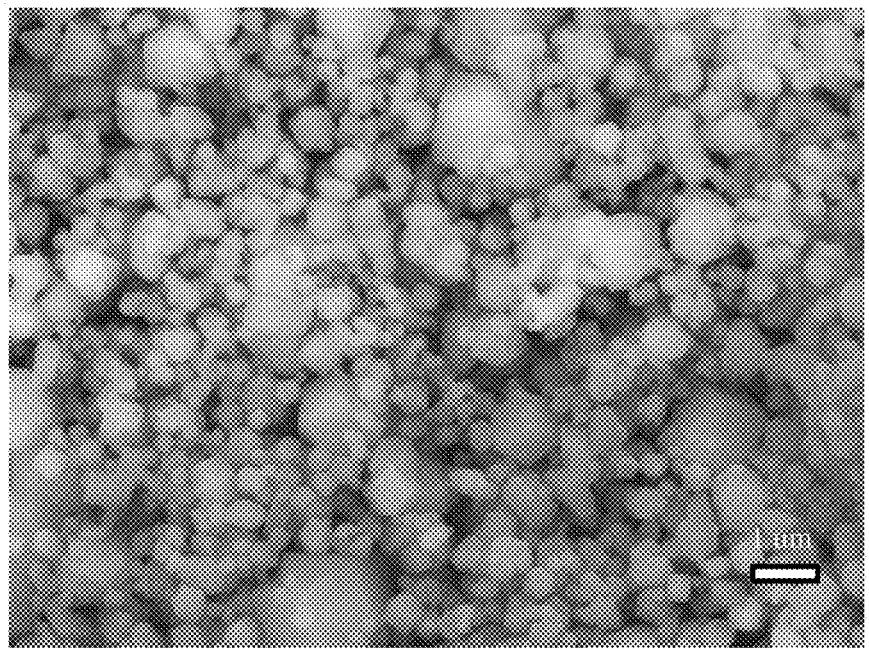
FIG. 9 is SEM image of ZIF-90 synthesized by example 8 of the present invention.

Zinc nitrate (371 mg) is dissolved in isobutyl alcohol (12.5 mL) as a first solution, wherein isobutyl alcohol is served as an auxiliary agent. ICA (480 mg) and PVP (500 mg) were added into deionized water (12.5 mL) as a second solution. Then, the first solution is gradually added into the second solution at room temperature, and the mixed solution is stirred and reacted to obtain a precipitate powder. In the present example, the molar ratio of $Zn^{2+}$:ICA is 1:4. The resulting powder is collected by centrifugation, washed with methanol several times, and vacuum dried at 50° C. to obtain ZIF-90 (70 mg). The SEM image of the obtained ZIF-90 with particle size of 430 nm is shown in FIG. 9.

Example 9

Figure 10:
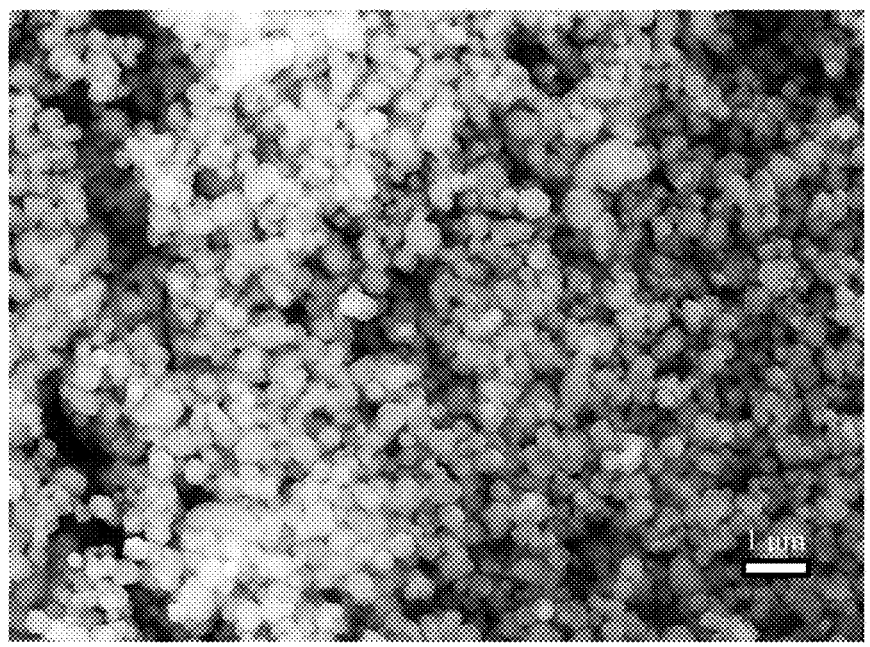
FIG. 10 is SEM image of ZIF-90 synthesized by example 8 of the present invention.

Zinc nitrate (371 mg) is dissolved in tert-butyl alcohol (12.5 mL) as a first solution, wherein tert-butyl alcohol is served as an auxiliary agent. ICA (480 mg) and PVP (500 mg) were added into deionized water (12.5 mL) as a second solution. Then, the first solution is gradually added into the second solution at room temperature, and the mixed solution is stirred and reacted to obtain a precipitate powder. In the present example, the molar ratio of $Zn^{2+}$:ICA is 1:4. The resulting powder is collected by centrifugation, washed with methanol several times, and vacuum dried at 50° C. to obtain ZIF-90 (70 mg). The SEM image of the obtained ZIF-90 with particle size of 275 nm is shown in FIG. 10.

Figure 11:
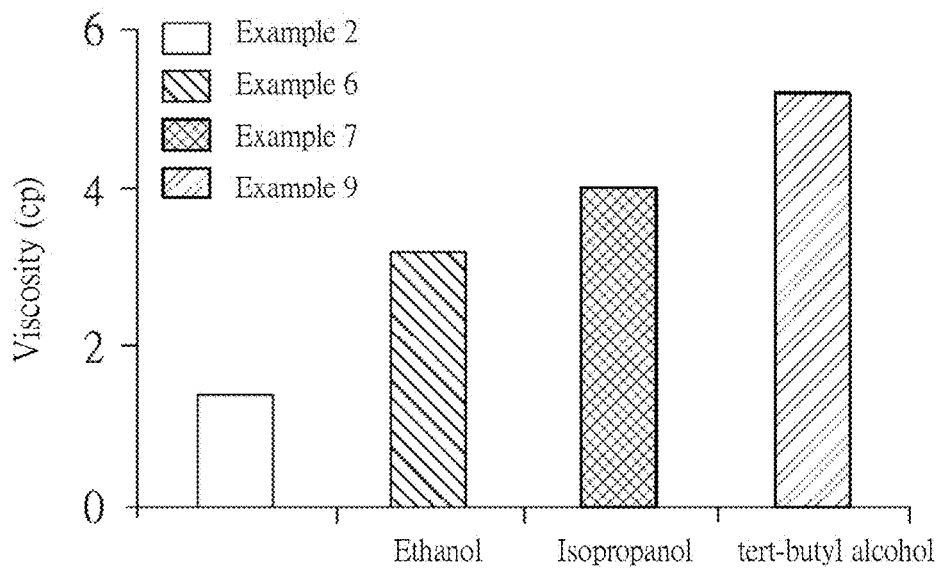
FIG. 11 is a diagram of the viscosities of the reactive solutions of examples 2, 6, 7, and 9 of the present invention.
Figure 12:
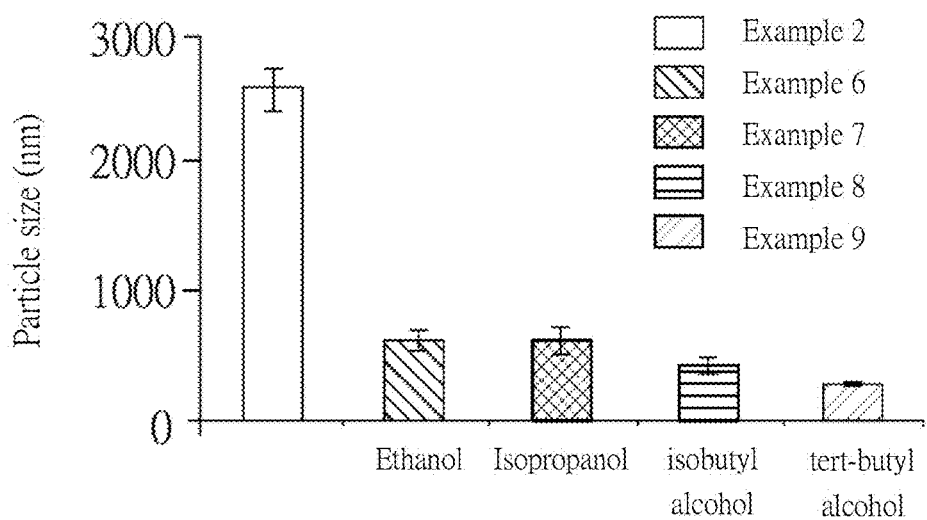
FIG. 12 is a diagram of the average particle size of ZIF-90 synthesized by example.

Referring now to FIG. 11, FIG. 11 shows the viscosity of the reactive solutions of examples 6, 7, and 9, in which the auxiliary is added respectively for the reactions, and the viscosity of the reactive solution of example 2 as comparative example. The measurement of viscosity is carried out by cone and plate method using Brookfield DV-III Ultra Programmable Rheometer. According to the results shown in FIG. 11, the viscosity of the reactive solution increased as the number of carbons in the alcohol increased. For example, when no alcohol is added as the auxiliary agent, the viscosity of the reactive solution is about 1.5 cp; when ethanol is added as the auxiliary agent (number of carbons=2), the viscosity of the reactive solution increases to about 3 cp; and when tert-butyl alcohol is added as the auxiliary agent (number of carbons=4), the viscosity of the reactive solution further increases to about 5 cp. Refer to FIG. 12, which shows the corresponding diagram of particle sizes of the ZIF-90 synthesized with different auxiliaries. When alcohol is used as the auxiliary agent for the reaction, the particle size of the synthesized ZIF-90 decreased as the carbon number of the auxiliary agent increased. For example, when tert-butyl alcohol is used as the auxiliary agent, the particle size of the synthesized ZIF-90 is 275 nm. With the micro-nano scaled ZIF-90, the specific surface area of the pores in ZIF-90 is significantly increased. Accordingly, in the present invention, ZIF-90 with different particle sizes can be synthesized by the addition of the additives or the auxiliary agents. ZIF-90 with uniform size is obtained by adding the additive PVP, and ZIF-90 with different particle size can be obtained. Therefore, the applicability of ZIF-90 is significantly increased. In addition, the preparation method provided by the present invention uses water as the solvent for the reaction, thus significantly reduced the impact to the environment.

Although the present invention has been explained in relation to its preferred embodiment, it is to be understood that many other possible modifications and variations can be made without departing from the spirit and scope of the invention as hereinafter claimed.

What is claimed is:

1. A preparation method of zeolitic imidazolate framework-90 (ZIF-90) in water-based system, comprising: mixing a first solution comprising a zinc compound and a second solution comprising an imidazole compound at room temperature to provide a reactive solution; and reacting the reactive solution to obtain a zeolitic imidazolate framework;
wherein the first solution further comprises an auxiliary agent which is at least one selected from the group of $C_{1-6}$ alcohol, the imidazole compound in the second solution is imidazole-2-carboxaldehyde (ICA), the second solution further comprises an additive, and the additive is polyvinylpyrrolidone (PVP).

2. The preparation method as claimed in claim 1, wherein the zinc compound in the first solution is at least one selected from the group consisting of Zn(NO3)2, Zn(OH)2, Zn(Ac)2, and ZnCl2.

3. The preparation method as claimed in claim 1, wherein the concentration of the zinc compound in the first solution is 0.02 to 0.8 M.

4. The preparation method as claimed in claim 1, wherein the concentration of the imidazole compound in the second solution is 0.1 to 1 M.

5. The preparation method as claimed in claim 1, wherein a molar ratio of a zinc ion ionized from the zinc compound to the imidazole compound is 1:1 to 1:80.

6. The preparation method as claimed in claim 1, wherein a content of the additive in the reactive solution is 0.1 to 10 wt %.

7. The preparation method as claimed in claim 1, wherein an average particle size of the ZIF-90 is 100 to 4000 nm.

* * * * *